United States Patent
Yeh et al.

(10) Patent No.: US 9,810,640 B2
(45) Date of Patent: Nov. 7, 2017

(54) PANEL INSPECTION APPARATUS AND METHOD

(71) Applicant: CHENG MEI INSTRUMENT TECHNOLOGY CO., LTD., Zhubei (TW)

(72) Inventors: Chao-Yi Yeh, Zhubei (TW); Pin-Chuan Su, Zhubei (TW); Shang-Iun Yang, Zhubei (TW); Chih Yuan Liu, Zhubei (TW)

(73) Assignee: CHENG MEI INSTRUMENT TECHNOLOGY CO., LTD., Zhubei (TW)

( * ) Notice: Subject to any disclaimer, the term of this patent is extended or adjusted under 35 U.S.C. 154(b) by 44 days.

(21) Appl. No.: 15/006,976

(22) Filed: Jan. 26, 2016

(65) Prior Publication Data
US 2016/0216214 A1    Jul. 28, 2016

Related U.S. Application Data

(60) Provisional application No. 62/108,378, filed on Jan. 27, 2015.

(51) Int. Cl.
*G01N 21/00* (2006.01)
*G01N 21/89* (2006.01)
(Continued)

(52) U.S. Cl.
CPC ..... *G01N 21/8914* (2013.01); *G01N 21/8806* (2013.01); *G01N 2021/8841* (2013.01);
(Continued)

(58) Field of Classification Search
CPC ....... G01N 2021/9513; G01N 21/9501; G01N 21/9503; G01N 2021/95676;
(Continued)

(56) References Cited

U.S. PATENT DOCUMENTS 5,132,791 A * 7/1992 Wertz .................. B65H 43/04
                                                    250/559.46
5,245,403 A * 9/1993 Kato .................... G01N 21/94
                                                    250/559.09
(Continued)

FOREIGN PATENT DOCUMENTS

CN         201576122 U    9/2010
CN           1954204 B    3/2011
(Continued)

OTHER PUBLICATIONS

First Office Action issued in Taiwan and its English Summary, TW Application No. 105101057, dated Oct. 5, 2016, 8 pgs.

*Primary Examiner* — Michael P Stafira
(74) *Attorney, Agent, or Firm* — Christensen, Fonder, Dardi & Herbert PLLC (57) ABSTRACT

A panel inspection apparatus is provided. The panel inspection apparatus has a support platform, a delivery platform and a panel inspection assembly. The delivery platform is disposed on the support platform, and the delivery platform has a push module for delivering the panel. The panel inspection assembly includes a plurality of light source modules and a plurality of image-taking modules corresponding to the light source modules. The light source modules include a front light source, a first horizontal light source, and a back light source. The image-taking modules include a front light image-taking module, a first horizontal light image-taking module, and a back light image-taking module. The push module delivers the panel across the support platform so that a plurality of light beams emitted from the light source modules can scan the panel to finish the panel inspection process.

19 Claims, 9 Drawing Sheets

(51) Int. Cl.
*G01N 21/88* (2006.01)
*G01N 21/95* (2006.01)

(52) U.S. Cl.
CPC .............. *G01N 2021/9513* (2013.01); *G01N 2201/103* (2013.01)

(58) Field of Classification Search
CPC .. G01N 21/8806; G01N 21/896; G01N 21/94; G01N 21/55; G01N 21/95; G01N 21/958; G01N 2201/062; G01N 25/72; G01N 2021/95638
See application file for complete search history.

(56) References Cited

U.S. PATENT DOCUMENTS

| | | | |
|---|---|---|---|
| 5,355,213 A * | 10/1994 | Dotan | G01N 21/8806 356/124 |
| 5,701,178 A * | 12/1997 | Burns | G01B 11/06 356/394 |
| 5,714,998 A * | 2/1998 | Wheeler | B07C 5/3422 348/127 |
| 6,437,357 B1 * | 8/2002 | Weiss | G01N 21/896 250/223 R |
| 7,084,970 B2 | 8/2006 | Weiss et al. | |
| 7,787,010 B2 | 8/2010 | DiFrancesco | |
| 8,290,624 B2 | 10/2012 | Hjornet | |
| 8,413,308 B2 | 4/2013 | Ku | |
| 2010/0040277 A1 * | 2/2010 | Kao | G01N 21/86 382/141 |
| 2010/0207854 A1 | 8/2010 | Chen et al. | |

FOREIGN PATENT DOCUMENTS

| | | |
|---|---|---|
| CN | 102368138 A | 3/2012 |
| CN | 202898515 U | 4/2013 |
| TW | 201445133 A | 12/2014 |
| WO | WO 2011/073846 A1 | 6/2011 |

* cited by examiner

PANEL INSPECTION APPARATUS AND METHOD

This application claims the benefit of U.S. Provisional Application No. 62/108,378, filed Jan. 27, 2015.

CROSS-REFERENCES TO RELATED APPLICATIONS

Not applicable.

BACKGROUND OF THE INVENTION

Field of the Invention

The present invention relates to a panel inspection apparatus, and more particularly, relates to a panel inspection apparatus capable of continuously inspecting an upper surface, a lower surface, two horizontal side surfaces and two vertical side surfaces of each of a plurality of panels.

Descriptions of the Related Art

With the improvement of the consumer display apparatus technology and the growing demand for consumer display apparatuses, the display effect of display apparatuses such as mobile phones, tablet computers and televisions needs to be improved correspondingly. In addition to the high-end panel manufacturing technology, inspection of the panel products is further used as a key means to improve the value of the products.

Panels are often subjected to cleaning, cutting or delivering procedures during the manufacturing process, so defects such as smudges, cracks, scratches, or scraps are likely to be generated on the surface or at the periphery of a panel. If the aforesaid defects fail to be found by the inspection personnel in the early-stage inspection process of the panel, then not only the yield of the subsequently assembled product will be decreased, but the backend mechanical equipment used in the assembling process may also be damaged due to the aforesaid defects of the panel.

Thus, in order to inspect surfaces of the panel, i.e., an upper surface, a lower surface and four side surfaces (i.e., a front side surface, a back side surface, a left side surface and a right side surface), the inspection equipment performs inspection in a section-by-section manner on different surfaces of the panel to obtain relevant inspection results in the current inspection process. Moreover, some mechanical equipment adopts several mechanical arms to transfer the to-be-tested object (i.e., the panel) and also to obtain information of the aforesaid surfaces by turning over the object or changing the working region with the mechanical arms.

On the other hand, in addition to the optical technology, other physical inspection methods may also be adopted to obtain information of the surfaces of the panel. However, although a highly accurate inspection result may be obtained through the various physical inspection methods, the inspection time is prolonged and the possibility that the panel might be damaged in the inspection process is increased because most of the inspection equipment performs inspection in a section-by-section manner or through complicated procedures.

Accordingly, an urgent need exists in the art to provide a one-time panel inspection process, which can inspect all surfaces of a panel in a single inspection process to improve the inspection efficiency and reduce the damage to the panel.

SUMMARY OF THE INVENTION

An objective of the present invention is to provide a single-pass (or one-time) panel inspection apparatus and panel inspection method to improve the inspection efficiency and the inspection yield of the panel and reduce the damage to the panel.

To achieve the aforesaid objective, a panel inspection apparatus provided according to the present invention comprises a support platform, a delivery platform and a panel inspection assembly. The delivery platform is disposed on the support platform and has a push module. The panel inspection assembly has a plurality of light source modules and a plurality of image-taking modules corresponding to the light source modules. The light source modules comprise a front light source, a first horizontal light source, and a back light source, the image-taking modules comprise a front light image-taking module, a first horizontal light image-taking module, and a back light image-taking module, and the push module is adapted to push the panel across the support platform so that a plurality of light beams emitted from the light source modules can scan the panel for inspection.

To achieve the aforesaid objective, the light beams emitted by the panel inspection apparatus of the present invention comprise a front light beam, a first horizontal light beam, and a back light beam, and the front light source, the first horizontal light source and the back light source are adapted to emit the front light beam, the first horizontal light beam and the back light beam respectively.

To achieve the aforesaid objective, the light source modules comprised in the panel inspection apparatus of the present invention further comprise an oblique light source for emitting an oblique light beam, and the image-taking modules further comprise an oblique light image-taking module disposed corresponding to the oblique light source to receive the oblique light beam reflected by the panel.

To achieve the aforesaid objective, the panel of the present invention has an upper surface, a lower surface, two horizontal side surfaces and two vertical side surfaces.

To achieve the aforesaid objective, the support platform comprised in the panel inspection apparatus of the present invention has two alignment modules for aligning the panel with respect to the support platform.

To achieve the aforesaid objective, the push module comprised in the panel inspection apparatus of the present invention has two push devices that abut against two opposite vertical side edges of the panel and cooperate to push the panel at a constant speed.

To achieve the aforesaid objective, the push module comprised in the panel inspection apparatus of the present invention has two push devices that abut against two opposite vertical side edges of the panel and cooperate to push the panel at a variable speed.

To achieve the aforesaid objective, the push module comprised in the panel inspection apparatus of the present invention further comprises a plurality of second horizontal light sources for emitting a second horizontal light beam respectively, and when the panel is pushed by the push module, the horizontal light beams are adapted to irradiate two opposite side edges of the panel.

To achieve the aforesaid objective, the second horizontal light sources comprised in the panel inspection apparatus of the present invention are embedded into the two push devices.

To achieve the aforesaid objective, the second horizontal light sources comprised in the panel inspection apparatus of the present invention are linear light sources.

To achieve the aforesaid objective, the delivery platform comprised in the panel inspection apparatus of the present invention defines a plurality of working regions, and at least one gap is disposed between any two adjacent ones of the working regions to allow the light beams emitted by the light source modules to pass therethrough.

To achieve the aforesaid objective, a plurality of air-floating devices are disposed on the support platform comprised in the panel inspection apparatus of the present invention so that the panel stays in an air-floated state all the time during the inspection process.

To achieve the aforesaid objective, the at least one gap comprised in the panel inspection apparatus of the present invention comprises a first gap, a second gap and a third gap that allow the light beams emitted by the light source modules to pass therethrough respectively.

To achieve the aforesaid objective, the front light source, the back light source and/or the oblique light source of the light source modules comprised in the panel inspection apparatus of the present invention are linear light sources.

The present invention also includes a panel inspection method, which comprises the following steps of: (a) providing a delivery platform on a support platform; (b) providing a panel to the delivery platform; (c) aligning the panel by using an alignment module; (d) providing a push module and using the push module to push the panel; (e) providing a plurality of light source modules for emitting a plurality of light beams to the panel during the process of using the push module to push the panel; and (f) using a plurality of image-taking modules to take a plurality of images formed by the light beams when being reflected by the panel or a plurality of images formed by the light beams when passing through the panel to finish the inspection process.

To achieve the aforesaid objective, the image-taking modules comprised in the panel inspection method of the present invention are adapted to take the images formed by the light beams when being reflected by a plurality of surfaces of the panel.

To achieve the aforesaid objective, the plurality of surfaces of the panel of the present invention are an upper surface, a lower surface, two horizontal side surfaces and two vertical side surfaces.

To achieve the aforesaid objective, the push module comprised in the panel inspection method of the present invention pushes the panel at a constant speed in an air-floated state.

To achieve the aforesaid objective, the push module comprised in the panel inspection method of the present invention pushes the panel at a variable speed in an air-floated state.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

A panel inspection apparatus of the present invention is adapted to inspect a panel to ensure the yield of a subsequently assembled product (e.g., an intelligent mobile phone or a tablet computer).

Figure 1:
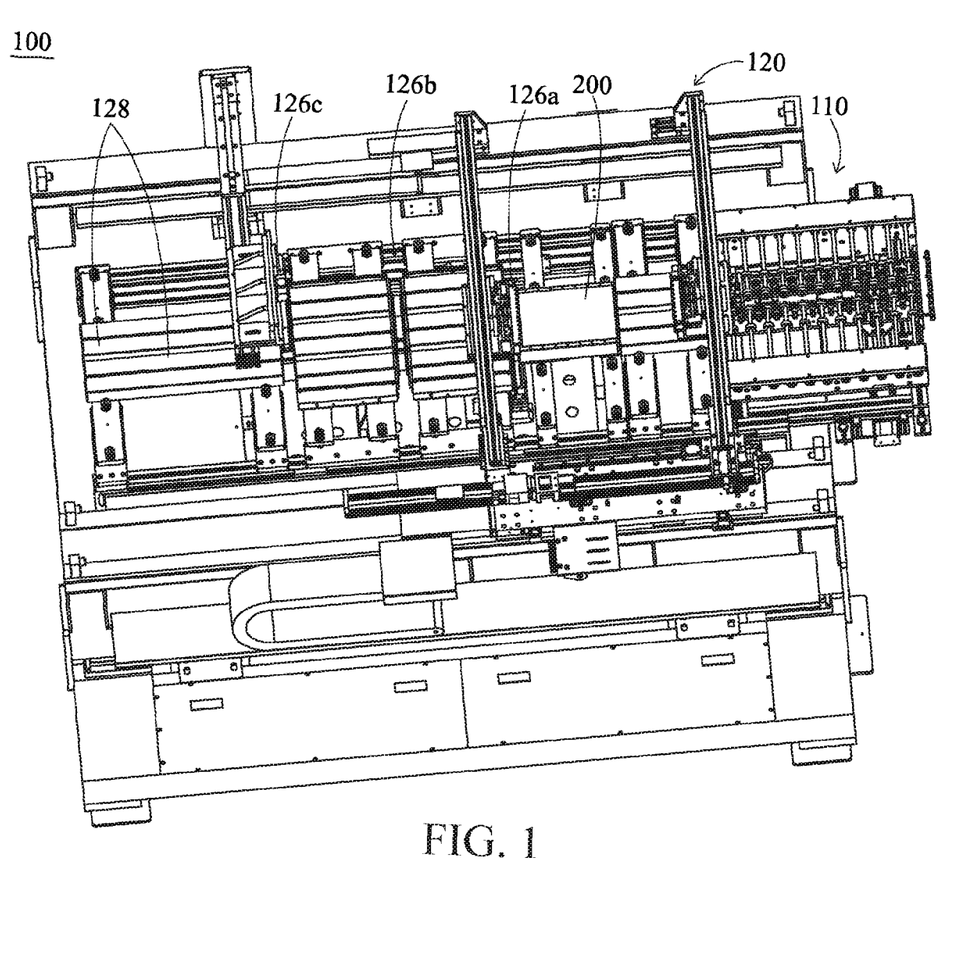
FIG. 1 is a perspective view of a panel inspection apparatus of the present invention.
Figure 2:
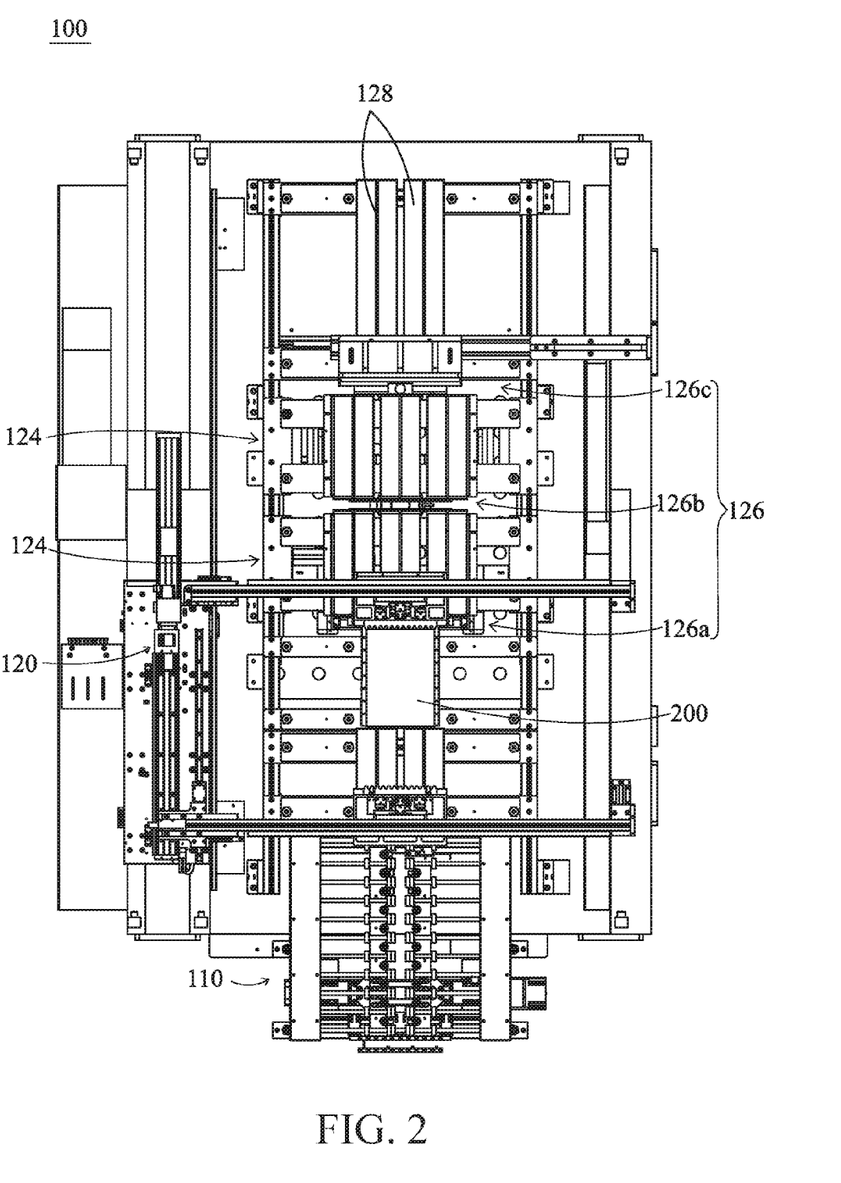
FIG. 2 is a top view of a panel inspection apparatus of the present invention.

As shown in FIG. 1 and FIG. 2, a panel inspection apparatus 100 for inspecting a panel 200 of the present invention comprises a support platform 110, a delivery platform 120 and a panel inspection assembly 130. The delivery platform 120 is disposed on the support platform 110 and has a push module 122. The panel inspection assembly 130 has a plurality of light source modules 140 and a plurality of image-taking modules 150 corresponding to the light source modules 140. In this way, the push module 122 of the delivery platform 120 is adapted to push the panel 200 across the support platform 110 so that a plurality of light beams emitted from the light source modules 140 can scan surfaces of the panel 200 for relevant inspection.

In detail, because of the widespread use of mobile devices and the demand for a low profile thereof, strict specifications have been established on parameters (e.g., surface flatness, surface curvature, surface scratches, edge defects or the like) of the core element (i.e., a display panel or a touch panel) of a mobile device. Therefore, an upper surface 202, a lower surface 204 opposite to the upper surface 202, and two horizontal side surfaces 206 and two vertical side surfaces 208 at four edges of the panel 200 shall all satisfy strict quality requirements. With the panel inspection apparatus 100 of the present invention, the upper surface 202, the lower surface 204, the two horizontal side surfaces 206 and the two vertical side surfaces 208 of the aforesaid panel 200 can be inspected at the same time in a single-pass (or one-time) inspection process, thereby remarkably shortening the inspection time and effectively improving the inspection efficiency.

Constitution and operation of the panel inspection assembly 130 will first be described hereinafter.

Figure 3:
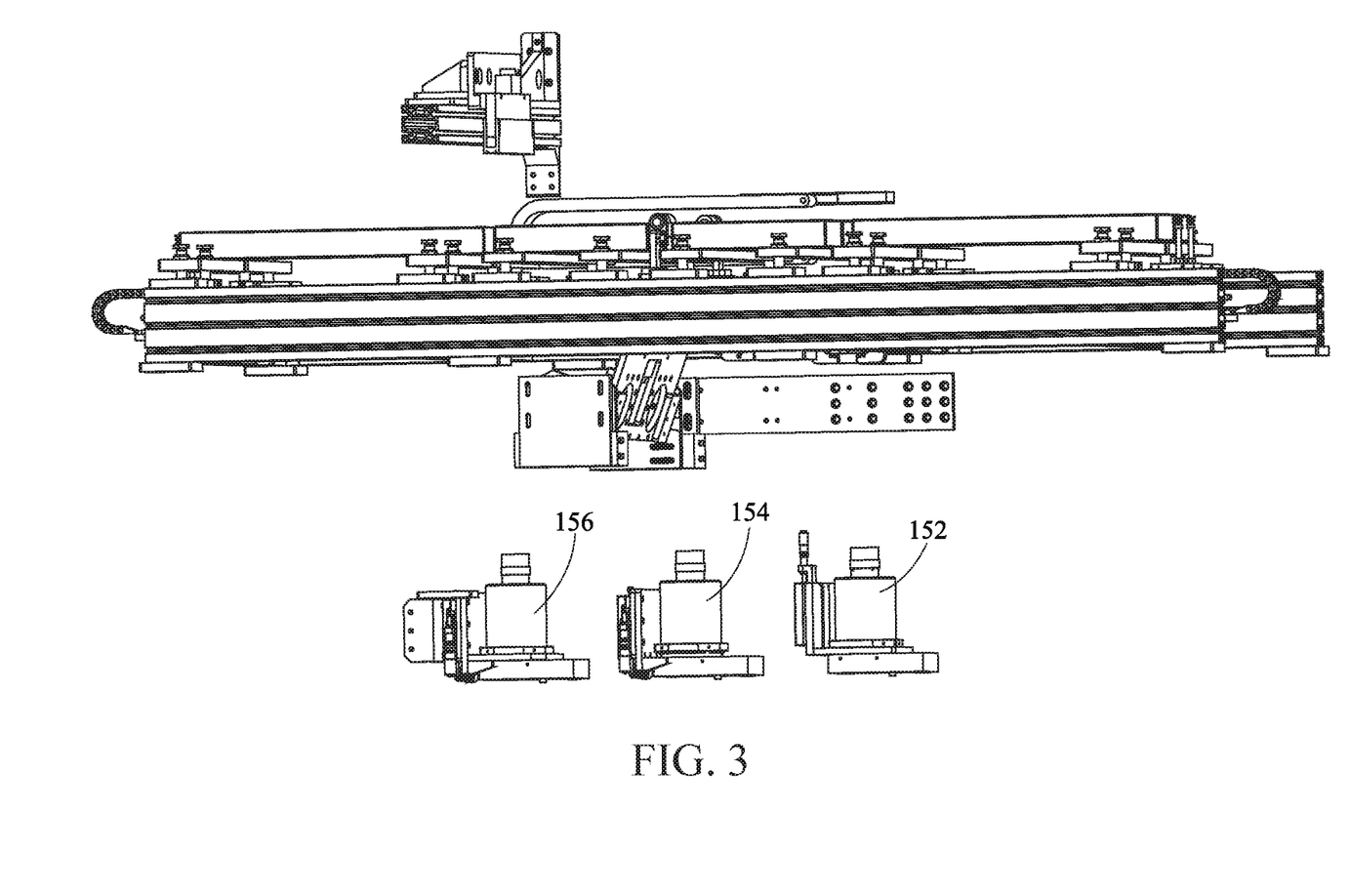
FIG. 3 is a schematic view illustrating the arrangement of a front light image-taking module, a first horizontal light image-taking module and a back light image-taking module of a panel inspection apparatus according to the present invention.
Figure 4:
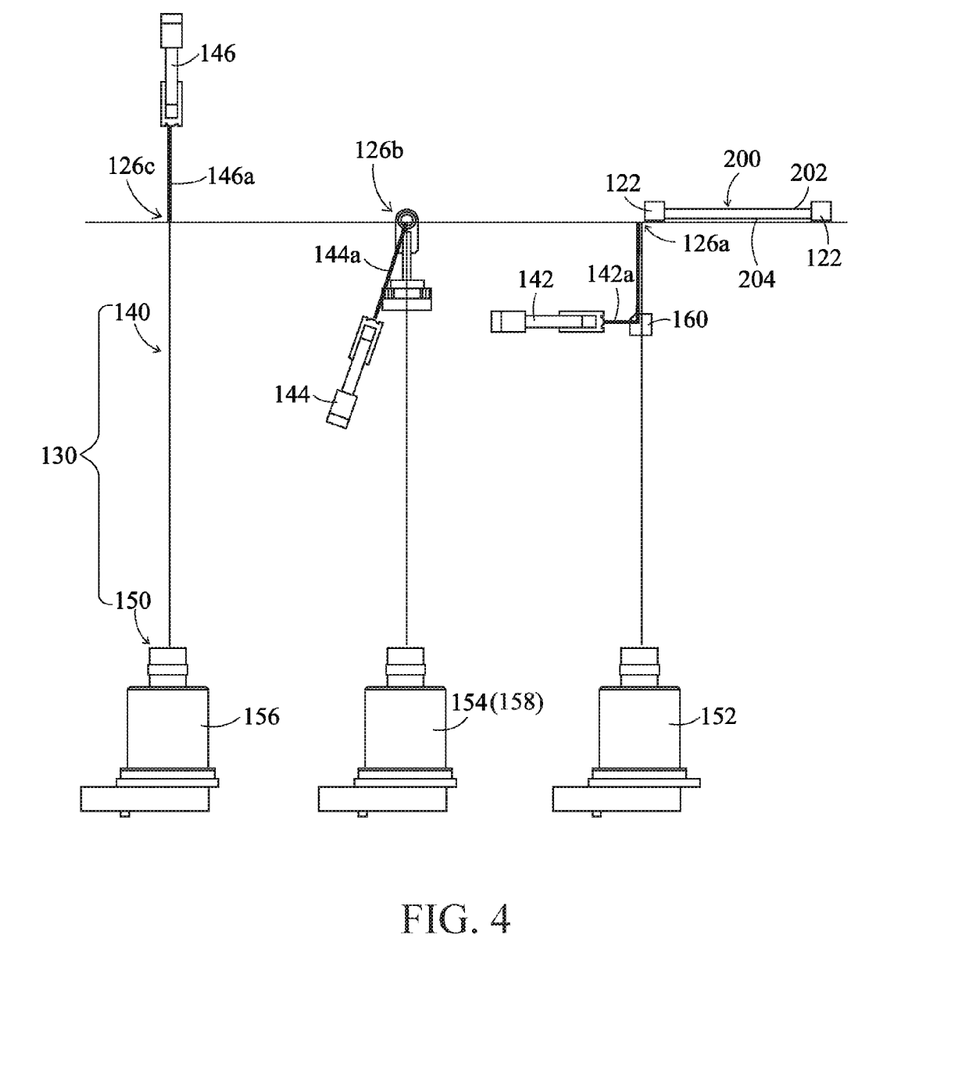
FIG. 4 is a schematic view illustrating the arrangement of a front light source, a first horizontal light source, and a back light source of a panel inspection apparatus according to the present invention.

As shown in FIG. 3 and FIG. 4, the light source modules 140 of the panel inspection assembly 130 comprise a front light source 142, a first horizontal light source 144 and a back light source 146, the image-taking modules 150 comprise a front light image-taking module 152, a horizontal light image-taking module 154, and a back light image-taking module 156. When the push module 122 pushes the panel 200 across the support platform 110, the light beams respectively emitted by the front light source 142, the first horizontal light source 144 and the back light source 146 are respectively received by the front light image-taking module 152, the horizontal light image-taking module 154, and the back light image-taking module 156 after being reflected by surfaces of the panel 200 or passing through the panel 200. Thereby, inspection personnel analyze according to received image information and obtain relevant inspection results of parameters of the panel 200.

Figure 7:
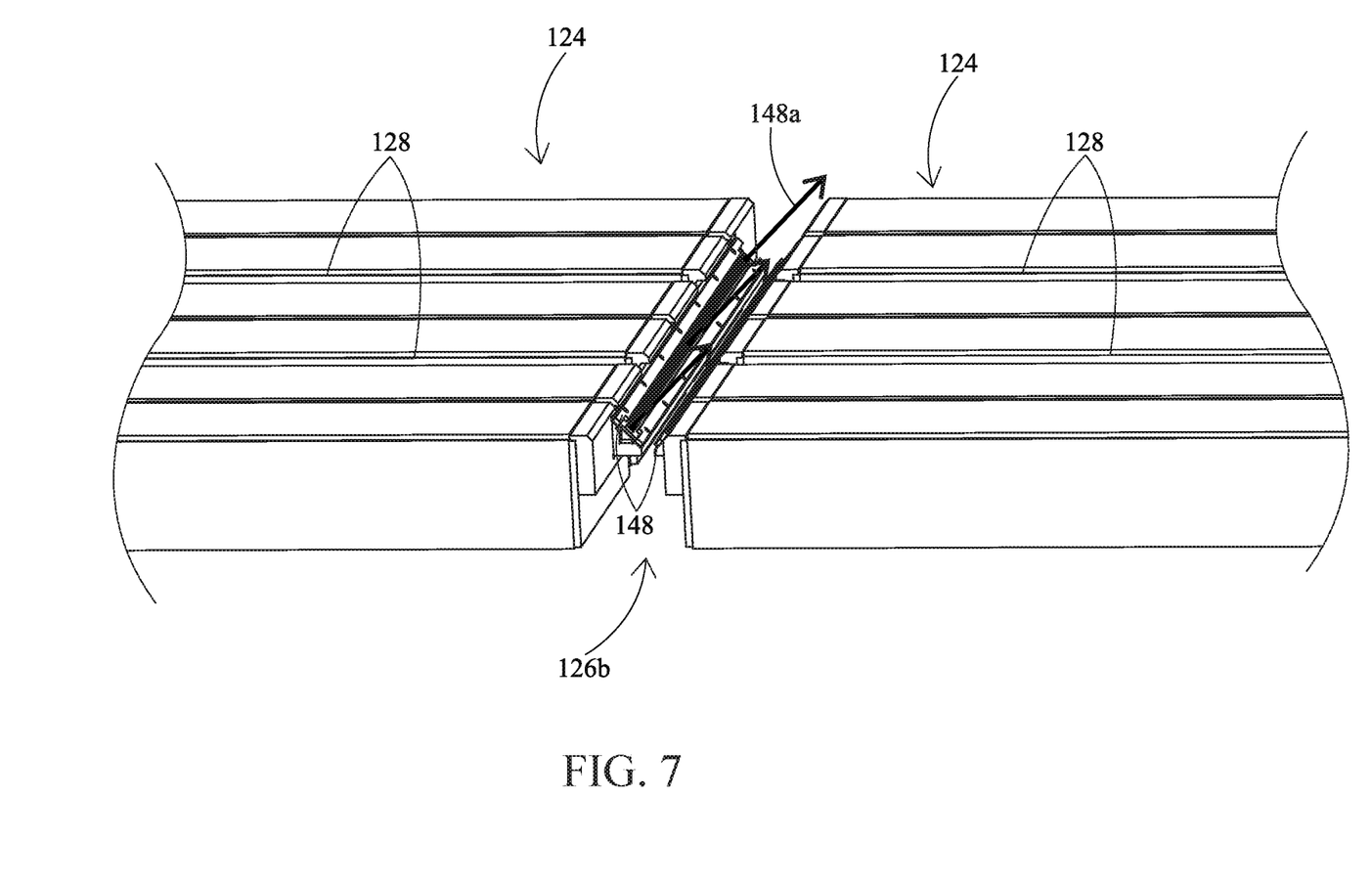
FIG. 7 is a schematic view of an oblique light source disposed at an angle of 45° in a panel inspection apparatus of the present invention.

In addition to the aforesaid front light source 142, the first horizontal light source 144 and the back light source 146, the light source modules 140 of the panel inspection assembly 130 may further comprise an oblique light source 148 as shown in FIG. 7, and the image-taking modules 150 further comprise an oblique light image-taking module 158. Therefore, a light beam emitted by the oblique light source 148 can be received by the oblique light image-taking module 158 after being reflected by the panel 200, thereby improving the quality of inspection (e.g., scratches inspection) for the panel 200.

In the practical inspection of the panel 200, the panel 200 may first be aligned with respect to the support platform 110 by means of two alignment modules (not shown) of the support platform 110 so as to ensure that a correct path is subsequently followed. Next, two push devices 122a of the push module 122 abut against two opposite side edges of the panel 200 (in this embodiment, the two side edges are two vertical side surfaces 208 of the panel 200 but are not limited thereto), and the two push devices 122a cooperate to push the panel 200 at a constant speed so that the panel 200 can be sequentially irradiated by the light beams respectively emitted by the front light source 142, the first horizontal light source 144 and the back light source 146, thereby finishing the inspection process for the panel 200 via the light beams that are reflected by or passing through the panel 200 and then received by the front light image-taking module 152, the horizontal light image-taking module 154, and the back light image-taking module 156.

Figure 5:
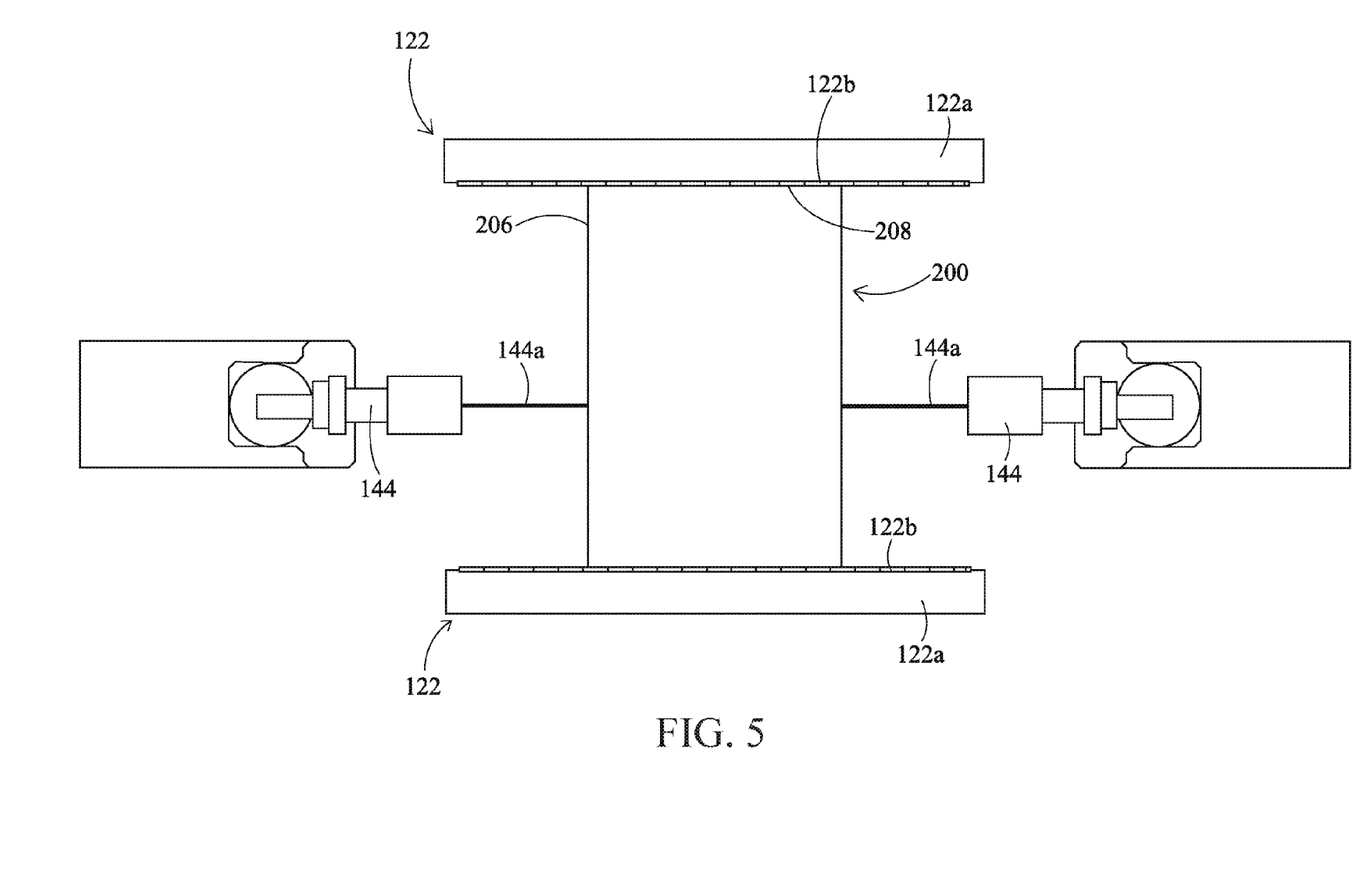
FIG. 5 and FIG. 6 are schematic views illustrating the arrangement of a first horizontal light source and a second horizontal light source of a panel inspection apparatus according to the present invention.
Figure 6:
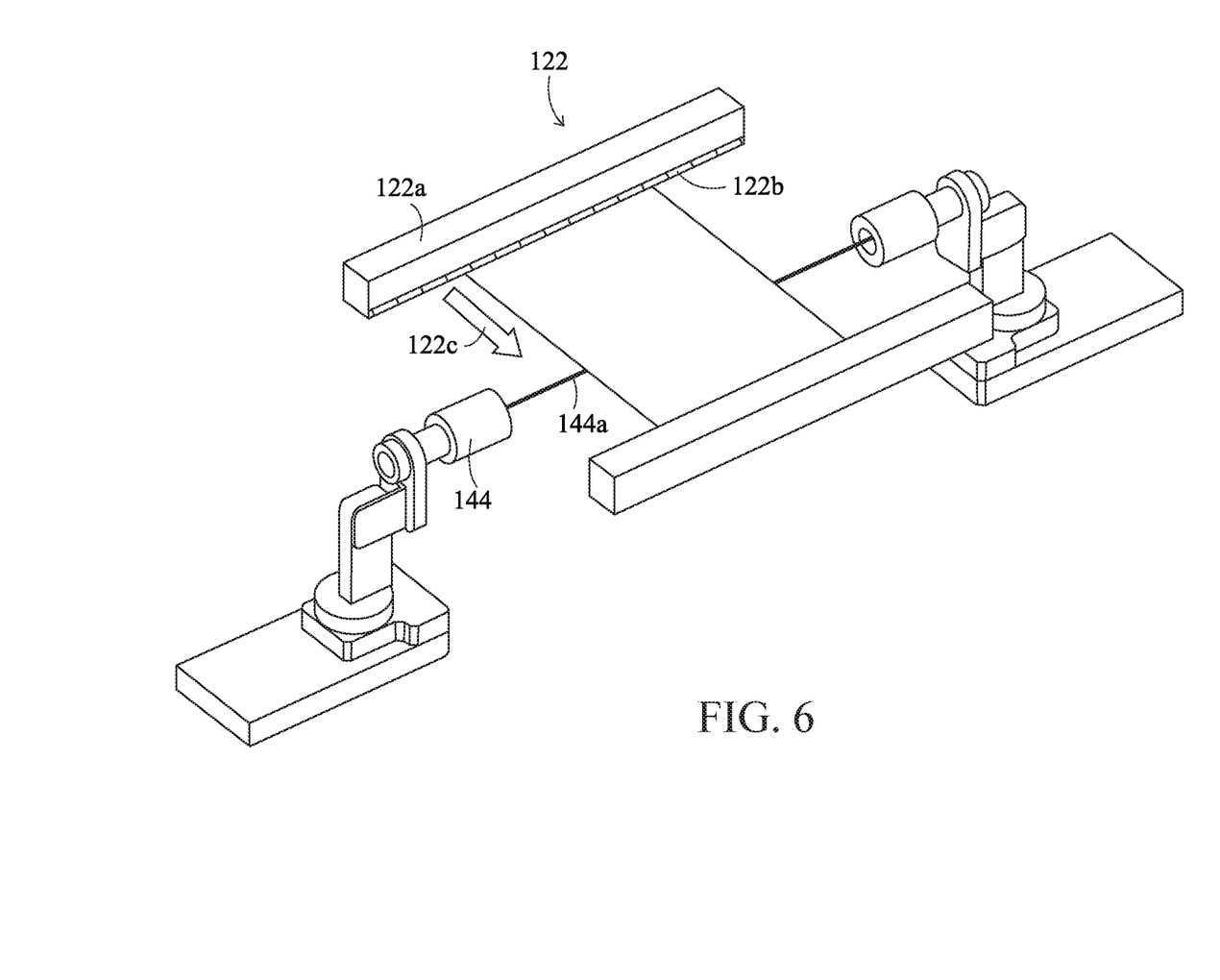

On the other hand, the push module 122 comprises a plurality of second horizontal light sources 122b so that each of the second horizontal light sources 122b may emit a second horizontal light beam 122c respectively for two side edges against which the push module 122 abuts (i.e., two vertical side surfaces 208 of the panel 200). In this way, when the panel 200 is pushed by the push devices 122a of the push module 122, the second horizontal light beams 122c emitted by the second horizontal light sources 122b are adapted to irradiate the two vertical side surfaces 208 of the panel 200, be reflected by the two vertical side surfaces 208 and then received by the horizontal light image-taking module 154, thereby finishing the relevant inspection process for the two vertical side surfaces 208.

In a preferred embodiment of the present invention, the aforesaid second horizontal light sources 122b are directly embedded into the two push devices 122a so that the two vertical side surfaces 208 of the panel 200 can still be irradiated by the second horizontal light sources 122b when the two push devices 122a are pushing the panel 200, and meanwhile, the possible light loss is avoided.

It shall be appreciated that, although the two push devices 122a cooperate to push the panel 200 at a constant speed in the aforesaid implementation, this is not limiting. In other words, through other appropriate arrangement and configuration of the light source modules 140 and the image-taking modules 150, e.g., by changing the arrangement sequence of the front light source 142, the first horizontal light source 144 and the back light source 146 with respect to the front light image-taking module 152, the horizontal light image-taking module 154, and the back light image-taking module 156, or by allowing the two push devices 122a to cooperate to push the panel 200 at a variable speed, the same or even better inspection effect or inspection speed can be achieved for the panel 200 in a single-pass push or inspection process.

In the present invention, the delivery platform 120 of the panel inspection apparatus 100 may define a plurality of working regions 124 to allow elements such as the front light source 142, the first horizontal light source 144, the back light source 146, the front light image-taking module 152, the horizontal light image-taking module 154, and the back light image-taking module 156 to be disposed therein. At least one gap 126 may be further disposed between any two adjacent ones of the working regions 124 to allow the light beams emitted by the light source modules 140 or the light beams reflected by the panel 200 to pass therethrough.

On the other hand, a plurality of air-floating devices 128 are disposed on the support platform 110 of the panel inspection device 100 to reduce the resistance and increase the speed at which the panel 200 is pushed by the push module 122. Thus, with the arrangement of the air-floating devices 128, the panel 200 can stay in an air-floated state all the time during the process in which the panel 200 is pushed by the push module 122 across the support platform 110 for inspection.

Still referring to FIG. 1 and FIG. 2, in a preferred embodiment of the present invention, the aforesaid at least one gap 126 comprises a first gap 126a, a second gap 126b and a third gap 126c that allow the light beams emitted by the light source modules 140 or the light beams reflected by the panel 200 to pass therethrough respectively, and thus these light beams can be received by the front light image-taking module 152, the horizontal light image-taking module 154, and the back light image-taking module 156 disposed below the support platform 110.

The arrangement relationships of the first gap 126a, the second gap 126b, and the third gap 126c with respect to the light source modules 140 and the image-taking modules 150 when the upper surface 202, the lower surface 204 and the two horizontal side surfaces 206 of the panel 200 are to be inspected will be described hereinafter in a preferred embodiment of the present invention.

First, the inspection process for the lower surface 204 of the panel 200 will be described.

As shown in FIG. 3 and FIG. 4, both the front light source 142 and the front light image-taking module 152 are disposed below the first gap 126a, and the front light source 142 is preferably disposed between the delivery platform 120 and the front light image-taking module 152. When the panel 200 is pushed across over the first gap 126a, a front light beam 142a emitted by the front light source 142 is adapted to be reflected by a mirror module 160 to pass through the first gap 126a from bottom to top and scan the lower surface 204 of the panel 200. Next, a lower surface image reflected after the lower surface 204 of the panel 200 is scanned by the front light beam 142a is taken by the front light image-taking module 152 disposed below through the first gap 126a, thereby finishing the inspection process for the lower surface 204 of the panel 200.

Next, the inspection process for the two horizontal side surfaces 206 of the panel 200 will be described.

As shown in FIG. 3 and FIG. 4, the horizontal light image-taking module 154 is disposed below the second gap 126b, and as shown in FIG. 5 and FIG. 6, the first horizontal light source 144 is located above the delivery platform 120 and disposed along two vertical side edges of the panel 200 in the advancing direction. When the panel 200 is pushed across over the second gap 126b, a first horizontal light beam 144a emitted by the first horizontal light source 144 is adapted to irradiate and scan the two horizontal side surfaces 206 of the panel 200 from two sides. Next, two horizontal side surface images reflected after the two horizontal side surfaces 206 of the panel 200 are scanned by the first horizontal light beam 144a can be taken by the horizontal light image-taking module 154 disposed below through the second gap 126b, thereby finishing the inspection process for the two horizontal side surfaces 206 of the panel 200.

Finally, the inspection process for the upper surface 202 of the panel 200 will be described.

Still referring to FIG. 3 and FIG. 4, the back light source 146 is disposed above the third gap 126c and the delivery platform 120, and the back light image-taking module 156 is disposed below the third gap 126c. When the panel 200 is pushed across over the third gap 126c, a back light beam 146a emitted by the back light source 146 is adapted to scan the upper surface 202 of the panel 200 from top to bottom. Next, an upper surface image generated after the upper surface 202 of the panel 200 is scanned by the back light beam 142c passes through the panel 200 so as to be taken by the back light image-taking module 156 disposed below through the third gap 126c, thereby finishing the inspection process for the upper surface 202 of the panel 200.

Therefore, with the arrangement and operation relationships of the first gap 126a, the second gap 126b, and the third gap 126c defined by the working regions 124 with respect to the light modules 140 and the image-taking modules 150, the upper surface image, the lower surface image and the two horizontal side surface images of the upper surface 202, the lower surface 204 and the two horizontal side surfaces 206 of the panel 200 can be respectively obtained in the single-pass process of pushing the panel 200, thereby finishing the inspection process for corresponding panel parameters.

On the other hand, in order to make the relevant panel inspection data more accurate, two oblique light sources 148 may further be disposed at two opposite sides in the second gap 126b, and each of the oblique light sources 148 inclines at a particular angle with respect to the delivery direction of the panel 200 as shown in FIG. 4 and FIG. 7. When an oblique light beam 148a emitted by the oblique light source 148 is incident at the particular angle from bottom to top and scans the upper surface 202 and the lower surface 204 of the panel 200, another upper/lower surface images reflected after the upper surface 202 and the lower surface 204 of the panel 200 are scanned by the oblique light beam 148a can be taken by the oblique light image-taking module 158 disposed below through the second gap 126b so as to finish another inspection process for the upper surface 202 and the lower surface 204 of the panel 200. Thereby, the errors possibly occurring when only the front light source 142 and/or the back light source 146 is used to inspect the panel 200 are avoided and meanwhile, the capability to inspect scratches on the upper/lower surfaces of the panel 200 is strengthened.

Figure 8:
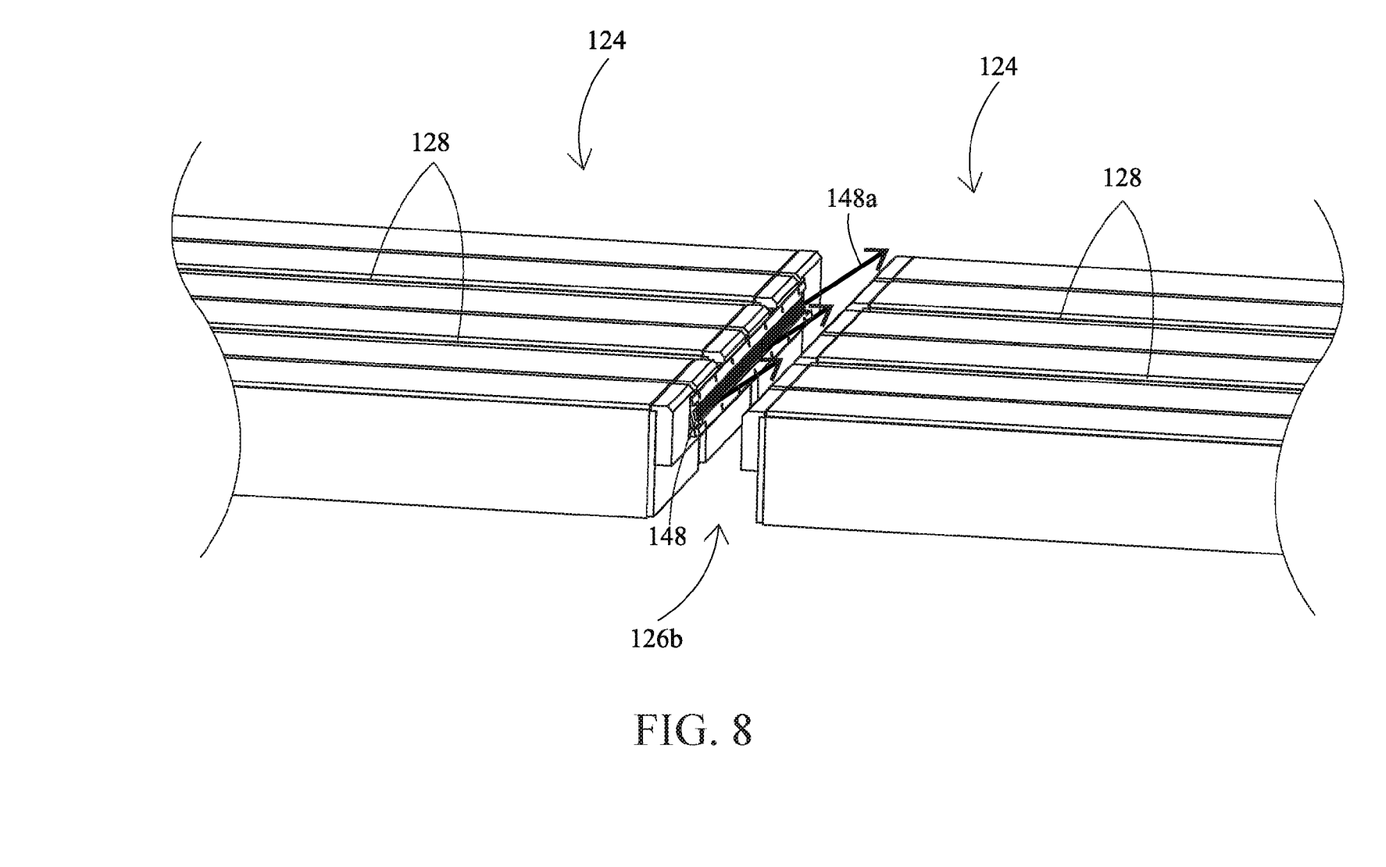
FIG. 8 is a schematic view of an oblique light source disposed at an angle of 14° in a panel inspection apparatus of the present invention.

The oblique angle of the oblique light source 148 is disposed as 45 degrees in the implementation of FIG. 7, and the oblique angle of the oblique light source 148 is disposed as 14 degrees in the implementation of FIG. 8; however, this is not limiting. Moreover, the aforesaid oblique light image-taking module 158 may be directly replaced by the horizontal light image-taking module 154 that is already disposed below the second gap 126b to reduce the construction cost of the panel inspection apparatus 100 of the present invention.

Although the aforesaid oblique light source 148 is disposed in the second gap 126b as an example, it may also be optionally disposed in the first gap 126a or the third gap 126c depending on different requirements of the inspection personnel.

Additionally, in a preferred implementation of the present invention, both the front light source 142 and the back light source 144 of the light source modules 140 are linear light sources so that an uniform front light beam 142a and back light beam 144a can be provided in the inspection process and respectively be emitted to the lower surface 204 and the upper surface 202 of the panel 200.

Figure 9:
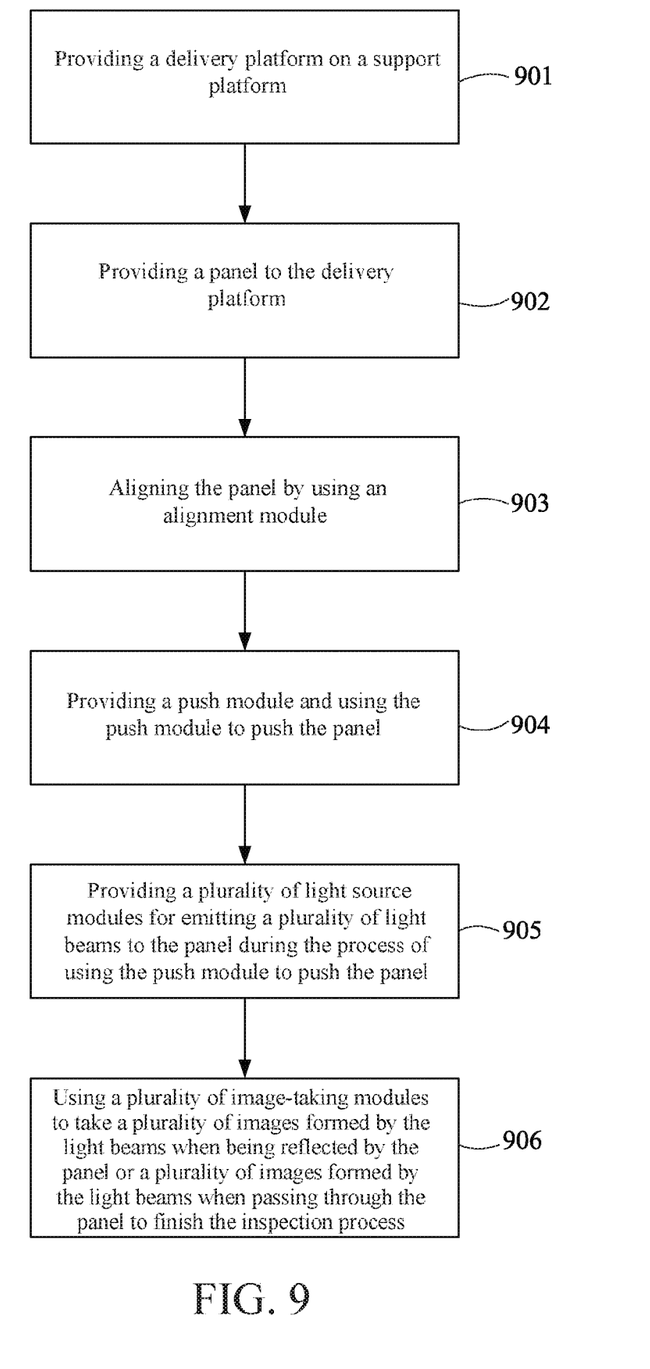
FIG. 9 is a flowchart diagram of a panel inspection method of the present invention.

As shown in FIG. 9, the present invention also discloses a panel inspection method which comprises the following steps of: first providing a delivery platform 120 on a support platform 110 as shown in step 901; then providing a panel 200 to the delivery platform 120 as shown in step 902; aligning the panel 200 by using an alignment module as shown in step 903; providing a push module 122 and using the push module 122 to push the panel 200 as shown in step 904; providing a plurality of light source modules 140 for emitting a plurality of light beams to the panel 200 during the process of using the push module 122 to push the panel 200 as shown in step 905; and finally using a plurality of image-taking modules 150 to take a plurality of images formed by the light beams when being reflected by the panel 200 or a plurality of images formed by the light beams when passing through the panel 200 to finish the inspection process.

Corresponding to the aforesaid panel inspection apparatus 100, in the panel inspection method of the present invention, the image-taking modules 150 are adapted to take a plurality of images formed by the light beams when being reflected by the surfaces (i.e., the lower surface 204, the two horizontal side surfaces 206 and the two vertical side surfaces 208) of the panel 200 or a plurality of images formed by the light beams after passing through the upper surface 202 of the panel 200 for the relevant inspection process.

Moreover, considering that most of panels used in the current electronic products or mobile devices are light and thin, the panels are likely to be inadvertently damaged in the panel inspection. Thus, in the panel inspection method of the present invention, a plurality of air-floating devices 114 are further disposed on the support platform 110; and in this way, the panel 200 can stay in an air-floated state all the time when the panel 200 is pushed by the push devices 122a of the push module 122. Since the panel 200 is pushed by the push devices 122a with almost no friction, the panel 200 can readily travel across the support platform 110 provided with the light source modules 140 and the image-taking modules 150 to effectively reduce the possibility that the panel 200 might be damaged.

On the other hand, because only two vertical side surfaces 208 abut against the push devices 122a in the inspection process for the panel 200, the upper surface 202, the lower surface 204 and the two horizontal side surfaces 206 except for the two vertical side surfaces 208 can be scanned and the images thereof can be taken respectively by the combination of the back light source 146 and the back light image-taking module 156, the combination of the first horizontal light source 144 and the horizontal light image-taking module 154, and the combination of the front light source 142 and the front light image-taking module 152 in a single-pass push process without being obstructed by any barrier or obstructions.

Additionally, similar to the aforesaid panel inspection apparatus 100, an oblique light source 148 may also be provided in the panel inspection method of the present invention for emitting an oblique light beam 148a to the panel 200, and thereby the possible errors in the inspection process for the panel 200 by only using the front light source 142 and/or the back light source 146 are avoided and meanwhile, the capability to inspect scratches on the upper/lower surfaces of the panel 200 is strengthened.

In this way, because the panel inspection method of the present invention can inspect the upper surface 202, the lower surface 204 and the two horizontal side surfaces 206 of the panel 200 at the same time in a single-pass (i.e., one-time) push process, better performance in terms of the inspection speed and the inspection quality can be achieved as compared to the prior art.

Moreover, even if the two vertical side surfaces 208 abut against the push devices 122a in the inspection process for the panel 200, the problem that the two vertical side surfaces 208 cannot be irradiated by light beams in the push process can still be solved because two second horizontal light sources 122b are embedded within the push module 122 having the push devices 122a. That is, with the arrangement of the two second horizontal light sources 122b, the panel inspection apparatus 100 of the present invention can still obtain two vertical side surface images through two second horizontal light beams 122c emitted from the two second horizontal light sources 122b to the two vertical side surfaces 208 in the case where the two vertical side surfaces 208 abut against the push devices. Then, the two vertical side surface images are taken by the horizontal light image-taking module 154 disposed below through the second gap 126b, thereby finishing the inspection process for the two vertical side surfaces 208 of the panel 200.

According to the above descriptions, the panel inspection apparatus and the panel inspection method of the present invention can inspect the upper surface 202, the lower surface 204, the two horizontal side surfaces 206 and the two vertical side surfaces 208 of the panel 200 at the same time in a single-pass push process of the panel 200 by means of the arrangement of the light source modules 140, the image-taking modules 150 and the air-floating devices 128. Thus, as compared to the inspection method of the prior art, the panel inspection apparatus and the panel inspection method of the present invention have an improved inspection efficiency and inspection yield and effectively reduce the damage to the panel in the inspection process.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A panel inspection apparatus for inspecting a panel, comprising:
   a support platform;
   a delivery platform, being disposed on the support platform and having a push module; and
   a panel inspection assembly, having a plurality of light source modules and a plurality of image-taking modules corresponding to the light source modules;
   wherein the light source modules comprise a front light source, a first horizontal light source, and a back light source, the image-taking modules comprise a front light image-taking module, a horizontal light image-taking module, and a back light image-taking module, and the push module is adapted to push the panel across the support platform so that a plurality of light beams emitted from the light source modules can pass through the panel or be reflected by the panel so as to scan the panel for inspection.

2. The panel inspection apparatus of claim 1, wherein the light beams comprise a front light beam, a first horizontal light beam, and a back light beam, and the front light source, the first horizontal light source and the back light source are adapted to emit the front light beam, the first horizontal light beam and the back light beam respectively.

3. The panel inspection apparatus of claim 1, wherein the light source modules further comprise an oblique light source for emitting an oblique light beam, and the image-taking modules further comprise an oblique light image-taking module disposed corresponding to the oblique light source to receive the oblique light beam reflected by the panel.

4. The panel inspection apparatus of claim 1, wherein the panel has an upper surface, a lower surface, two horizontal side surfaces and two vertical side surfaces.

5. The panel inspection apparatus of claim 1, wherein the support platform has two alignment modules for aligning the panel with respect to the support platform.

6. The panel inspection apparatus of claim 1, wherein the push module has two push devices that abut against two opposite vertical side edges of the panel and cooperate to push the panel at a constant speed.

7. The panel inspection apparatus of claim 1, wherein the push module has two push devices that abut against two opposite side edges of the panel and cooperate to push the panel at a variable speed.

8. The panel inspection apparatus of claim 1, wherein the push module further comprises a plurality of second horizontal light sources for emitting a second horizontal light beam respectively, and when the panel is pushed by the push module, the second horizontal light beams are adapted to irradiate two opposite side edges of the panel.

9. The panel inspection apparatus of claim 8, wherein the second horizontal light sources are embedded into the two push devices.

10. The panel inspection apparatus of claim 8, wherein the second horizontal light sources are linear light sources.

11. The panel inspection apparatus of claim 1, wherein the delivery platform defines a plurality of working regions, and at least one gap is disposed between any two adjacent ones of the working regions to allow the light beams emitted by the light source modules to pass therethrough.

12. The panel inspection apparatus of claim 11, wherein a plurality of air-floating devices are disposed on the support platform so that the panel stays in an air-floated state all the time during the inspection process.

13. The panel inspection apparatus of claim 11, wherein the at least one gap comprises a first gap, a second gap and a third gap that allow the light beams emitted by the light source modules to pass therethrough respectively.

14. The panel inspection apparatus of claim 3, wherein the front light source, the back light source and/or the oblique light source of the light source modules are linear light sources.

15. A panel inspection method for inspecting a panel, comprising the following steps of:
   (a) providing a delivery platform on a support platform;
   (b) providing the panel to the delivery platform;
   (c) aligning the panel by using an alignment module;
   (d) providing a push module and using the push module to push the panel;

(e) providing a plurality of light source modules for emitting a plurality of light beams to the panel during the process of using the push module to push the panel; and (f) using a plurality of image-taking modules to take a plurality of images formed by the light beams when being reflected by the panel or a plurality of images formed by the light beams when passing through the panel to finish the inspection process.

16. The panel inspection method of claim 15, wherein the image-taking modules are adapted to take the images formed by the light beams when being reflected by a plurality of surfaces of the panel.

17. The panel inspection method of claim 16, wherein the plurality of surfaces of the panel are an upper surface, a lower surface, two horizontal side surfaces and two vertical side surfaces.

18. The panel inspection method of claim 15, wherein a plurality of air-floating devices are disposed on the support platform so that the panel is pushed by the push module at a constant speed in an air-floated state.

19. The panel inspection method of claim 15, wherein a plurality of air-floating devices are disposed on the support platform so that the panel is pushed by the push module at a variable speed in an air-floated state.

* * * * *